(12) United States Patent
Collier

(10) Patent No.: US 10,470,387 B2
(45) Date of Patent: Nov. 12, 2019

(54) HYBRID TOMATO VARIETY H1766

(71) Applicant: H.J. Heinz Company Brands LLC, Pittsburgh, PA (US)

(72) Inventor: George Collier, Wheatley (CA)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 222 days.

(21) Appl. No.: 15/881,423

(22) Filed: Jan. 26, 2018

(65) Prior Publication Data

US 2019/0230881 A1    Aug. 1, 2019

(51) Int. Cl.
*A01H 5/08* (2018.01)
*A01H 6/82* (2018.01)

(52) U.S. Cl.
CPC .............. *A01H 5/08* (2013.01); *A01H 6/825* (2018.05)

(58) Field of Classification Search
None
See application file for complete search history.

(56) References Cited

U.S. PATENT DOCUMENTS

2017/0035014 A1*  2/2017  Collier .................... A01H 5/08

* cited by examiner

*Primary Examiner* — Stephen Uyeno
(74) *Attorney, Agent, or Firm* — Fitch, Even, Tabin & Flannery LLP

(57) ABSTRACT

Hybrid tomato variety 'H1766' is described. The tomato variety is a ground-culture hybrid tomato variety suitable for machine harvest, and is adaptable to the climactic conditions of regions such as Eastern USA, Portugal, Spain, and Italy.

24 Claims, 1 Drawing Sheet
(1 of 1 Drawing Sheet(s) Filed in Color)

HYBRID TOMATO VARIETY H1766

FIELD

This invention relates to the field of plant breeding. In particular, this invention relates to a new variety of tomato, *Solanum lycopersicum* variety denominated 'H1766'.

BACKGROUND

Breeding improved tomato varieties involves providing genetics that give an advantage to the grower, processor, consumer, or other members of the supply chain. The improvement may be in the form of field performance, disease resistance, factory performance, or a fruit quality characteristic. For a tomato variety to be suitable to be grown for processing, the variety must have a concentrated fruit setting and maturity, firm fruit, and sufficient rot tolerance to allow early fruit to remain rot-free while later fruit continues to develop and ripen.

Most commercial processing tomato varieties are hybrids resulting from a cross pollination of two true-breeding, inbred parents. Through the use of true-breeding lines, a hybrid is produced that often displays characteristics of each parent, and often demonstrates characteristics that are superior to either parent alone, or that allow a hybrid to mask inadequacies of the individual parents.

Processing tomato varieties combining resistance to *verticillium* wilt race 1 (*Verticillium* dahlia), *fusarium* wilt race 1 and 2 (*Fusarium oxysporum* pv *lycopersici*), root knot nematode (*Meloidogyne incognita*) and tomato spotted wilt virus (TSWV) are highly desirable in most climates around the world. Moreover, in humid regions such as Eastern North America, there is considerable disease pressure from bacterial diseases such as bacterial canker (*Clavibacter michiganenesis michaganensis*) and bacterial spot caused by various *Xanthomonas* species. Thus, varieties with resistance are in high demand by both growers and processors to ensure a productive crop cycle. Additionally, in recent years the industry has seen an increase in the presence of Late blight (*Phytopthora infestans*) which can have a devastating impact on the tomato crop.

An additional important contribution that tomatoes provide to the human diet is the antioxidant lycopene. Specifically, processed tomato products are the primary source of tomato intake in the US diet. Higher levels of lycopene are beneficial both from a nutritional standpoint and from a consumer perception and quality standpoint. Tomato varieties having higher levels of lycopene result in products with a deeper red color that can be considered an indicator of higher product quality. Thus, a tomato variety with a higher level of lycopene, and improved color in general can be valuable from both a nutritional standpoint and a quality standpoint. However, to be commercially viable, the tomato variety must perform acceptably in the field and factory as required by any other processing tomato variety.

Processing tomato quality parameters differ from those of fruit used in the fresh market. The processing characteristics are typically determined using a sample of hot-break tomato pulp or juice produced in a consistent manner to those familiar with the art. For example, a fixed mass of tomatoes may be cooked in a microwave oven for several minutes to halt any enzymatic breakdown of the sample, lost water is replaced, and the sample is pulped to remove skins and seed to produce a uniform juice sample. The juice sample can be analyzed for various quality parameters important to processing tomato including but not limited to gross viscosity measures such as juice Bostwick, soluble solids measures using a refractometer (° Brix), measures of acidity and pH, and measures of color (e.g. a Hunter a/b score). The value of these traits depends on the product that is being commercially produced by the processing factory. In some instances, a factory will put a higher value on a thick viscosity variety, whereas in other instances, a thin viscosity will make a superior product and is preferred.

SUMMARY

In order to meet these needs, the present invention provides the improved tomato variety 'H1766'; a variety that produces exceptional yields of uniform fruit and demonstrates an adaptability to humid growing conditions around the world. The variety 'H1766' has resistance to *verticillium* wilt race 1, *fusarium* wilt races 1 and 2, root knot nematode, tomato spotted wilt virus (TSWV). In addition 'H1766' also possesses resistance to bacterial spot, bacterial canker, late blight and intermediate resistance to early blight. The fruit of 'H1766' have strong internal color and an average fruit weight of 68 grams. 'H1766' presents an advantage over industry standard varieties such as H3402 in that it carries higher levels of resistance to bacterial spot, bacterial canker, early blight and late blight. Tolerance to fruit rot in 'H1766' is very good, allowing for once-over machine harvesting applications requiring extended field holding.

In one aspect, the present disclosure is directed to tomato seed designated as 'H1766' having ATCC Accession Number PTA-124676. In one aspect, the present disclosure is directed to a tomato plant and parts isolated therefrom produced by growing 'H1766' tomato seed. In another aspect, the present disclosure is directed to a tomato plant and parts isolated therefrom having all the physiological, morphological, and/or genetic characteristics of a tomato plant produced by growing 'H1766' tomato seed having ATCC Accession Number PTA-124676. In still another aspect, the present disclosure is directed to an $F_1$ hybrid tomato seed, plants grown from the seed, and leaves, ovules, pollen, fruit, cotyledons, embryos, meristems, anthers, roots, root tips, pistils, flowers, stems, calli, stalks, hypocotyl, and pericarps isolated therefrom having 'H1766' as a parent, wherein 'H1766' is grown from 'H1766' tomato seed having ATCC Accession Number PTA-124676.

In still another aspect, the present disclosure is directed to tomato seed having at least a first set of the chromosomes of tomato variety 'H1766', wherein representative seed is deposited under ATCC Accession Number PTA-124676. In another aspect, the present disclosure is directed to an $F_1$ hybrid tomato seed, methods of making $F_1$ hybrid tomato seed, plants grown from the seed, leaf, ovule, pollen, rootstock, scion, fruit, cotyledon, embryo, meristem, anther, root, root tip, pistil, flower, stem, calli, stalk, hypocotyla, pericarp, or portion thereof isolated therefrom having 'H1766' as a parent, wherein 'H1766' is grown from 'H1766' tomato seed having ATCC Accession Number PTA-124676. The disclosure is also directed to a method of producing a tomato plant derived from tomato variety 'H1766', including crossing a plant of tomato variety 'H1766' with another tomato plant. The method may further comprise harvesting seed from the $F_1$ hybrid tomato seed and/or crossing the $F_1$ hybrid tomato plant with itself or another plant to produce seed from a progeny plant.

Tomato plant parts include leaf, ovule, pollen, cell, rootstock, scion, fruit, cotyledon, embryo, meristem, anther, root, root tip, pistil, flower, stem, calli, stalk, hypocotyl, pericarp, the like, and any portion thereof. In another embodiment, the present disclosure is further directed to tomato fruit, stem, leaf, root, root tip, pollen, cell, rootstock, scion, ovule, seed, and flower, and any portion thereof, isolated from 'H1766' tomato plants. In another aspect, the present disclosure is further directed to tissue culture of regenerable cells derived from 'H1766' tomato plants. The disclosure is further directed to a tomato plant regenerated from tissue culture. In another aspect, the disclosure is directed to a protoplast produced from tissue culture and a plant regenerated from the protoplast. At least in some approaches, the plant regenerated from the tissue culture or protoplast has all of the characteristics of tomato variety 'H1766' listed in Table 1.

In another aspect, the disclosure is directed to a method for producing a plant part, which at least in one aspect is tomato fruit, and harvesting the plant part. The disclosure also is directed to vegetatively propagating a plant of tomato variety 'H1766' by obtaining a part of the plant and regenerating a plant from the plant part. At least in some approaches, the regenerated plant has all of the characteristics of tomato variety 'H1766' listed in Table 1.

In yet another aspect, the present disclosure is further directed to a method of selecting tomato plants by a) growing 'H1766' tomato plants wherein the 'H1766' plants are grown from tomato seed having ATCC Accession Number PTA-124676; and b) selecting a plant from step a). In another embodiment, the present disclosure is further directed to tomato plants, plant parts and seeds produced by the tomato plants, where the tomato plants are isolated by the selection method.

In another aspect, the present disclosure is further directed to a method of breeding tomato plants by crossing a tomato plant with a plant grown from 'H1766' tomato seed having ATCC Accession Number PTA-124676. In another aspect, the tomato plant of tomato variety 'H1766' is self-pollinated. In still another aspect, the present disclosure is further directed to tomato plants, tomato parts from the tomato plants, and seeds produced therefrom where the tomato plant is isolated by the breeding method.

In another aspect, the disclosure relates to a plant of tomato variety 'H1766' comprising a transgene and/or a single locus conversion, and any seeds or plant parts isolated therefrom. The disclosure also relates to methods for preparing a plant of tomato variety 'H1766' comprising a transgene and/or a single locus conversion.

BRIEF DESCRIPTION OF THE DRAWING

The patent or application file contains at least one drawing executed in color. Copies of this patent or patent application publication with color drawings will be provided by the office upon request and payment of the necessary fee.

The FIGURE illustrates the fruit and plant of 'H1766'.

DETAILED DESCRIPTION

Described herein is the new and distinct tomato variety named 'H1766' that was developed to provide a ground-culture hybrid tomato variety (i.e., not grown on stakes) that is suitable for machine harvest, and are adaptable to the climactic conditions of regions such as the Eastern USA, Portugal, Spain, and Italy.

Tomato plants of 'H1766' are resistant to *verticillium* wilt race 1, *fusarium* wilt races 1 and 2, root knot nematode, tomato spotted wilt virus, bacterial spot, bacterial canker, and late blight, with intermediate resistance to early blight. Plants are light green in color with a sprawling habit as compared to tomato varieties of the same market class. Fruit of 'H1766' are firm, very smooth, and medium in size (68 gram). Both internal and external color are strong. Fruit are also considered to have an extended field storage which delays the onset of fruit rots after reaching red ripe maturity.

Stability of Variety 'H1766'

The variety is uniform and stable within commercially acceptable limits. As is true with other tomato varieties, a small percentage of variants can occur within commercially acceptable limits for almost any characteristic during the course of repeated multiplication. However, no variants were observed during the two years in which the variety was observed to be uniform and stable.

TABLE 1

Characterization of tomato variety 'H1766' compared to 2 industry standards, 'H1015' and 'H3402'

| Character | H1766 | H3402 | H1015 |
|---|---|---|---|
| Seedling | | | |
| Anthocyanin in hypocotyl | Present | Present | Present |
| Habit of 3-4 Wk seedling | Normal | Normal | Normal |
| Mature Plant | | | |
| Height | 47 | 63 | 48 |
| Growth Type | Determinate | Determinate | Determinate |
| Form | Normal | Sprawling | Normal |
| Size of Canopy | Medium | Large | Medium |
| Habit | Sprawling | Sprawling | Sprawling |
| Stem | | | |
| Branching | Profuse | Profuse | Profuse |
| Branching at Cotyledon | Absent | Absent | Absent |
| # nodes below first inflorescence | 4-7 nodes | 4-7 nodes | 4-7 nodes |
| # nodes between early inflor ($1^{st}$-$2^{nd}$, $2^{nd}$-$3^{rd}$) | 1-2 nodes | 1-2 nodes | 1-2 nodes |
| # nodes between later inflorescence | 1-2 nodes | 1-2 nodes | 1-2 nodes |
| Pubescence on younger stems | Sparsely Hairy | Moderate | Sparse |
| Leaf | | | |
| Type | Tomato | Tomato | Tomato |
| Morphology | Compound with major and minor leaflets | Compound with major and minor leaflets | Compound with major, minor and sub minor leaflets |
| Margins of Major Leaflets | Shallowly Toothed | Shallowly Toothed | Shallowly Toothed |
| Marginal Rolling or Wiltiness | Slight | Moderate | Moderate |
| Onset of Leaflet Rolling | Midseason | Midseason | Early Season |
| Surface of Major Leaflets | Rugose | Rugose | Rugose |
| Pubescence: | Normal | Normal | Normal |
| Inflorescence | | | |
| Type | Forked | Forked | Forked |
| # flowers in inflorescence average | 6 | 5 | 6 |
| Leafy or "running" inflorescence | absent | absent | absent |
| Flower | | | |
| Calyx | Normal | Normal | Normal |
| Calyx-Lobes | Shorter than corolla | Shorter than corolla | Shorter than corolla |
| Corolla Color | Yellow | Yellow | Yellow |
| Style pubescence | Sparse | Sparse | Sparse |
| Anthers | Fused/Tubed | Fused/Tubed | Fused/Tubed |
| Fasciation | Absent | Absent | Absent |
| 1st flower of 2nd or 3rd Inflorescence | Absent | Absent | Absent |

TABLE 1-continued

Characterization of tomato variety 'H1766' compared to 2 industry standards, 'H1015' and 'H3402'

| Character | H1766 | H3402 | H1015 |
|---|---|---|---|
| Fruit | | | |
| Typical shape in longitudinal section | Blocky Oval | Blocky Oval | Blocky Oval |
| Shape of transverse section | Round | Round | Round |
| Shape of stem end | Indented | Indented | Indented |
| Shape of blossom end | Flat | Flat | Flat |
| Shape of pistil scar | Stellate | Dot | Dot |
| Abscission layer | Absent | Absent | Absent |
| Point of detachment fruit at harvest | At calyx | At calyx | At calyx |
| Length of pedicel (joint to calyx attachment) (cm) | n/a | n/a | n/a |
| Length of mature fruit (stem axis) (cm) | 6.1 | 5.7 | 5.5 |
| Diameter of fruit at widest point (cm) | 4.9 | 4.3 | 4.1 |
| Weight of Mature Fruit (g) | 68 | 57 | 68 |
| Number of Locules | 2-4 | 2-4 | 2-4 |
| Fruit Surface | Slightly Rough | Smooth | Smooth |
| Fruit Base Color (Mature Green Stage) | Medium Green | Medium Green | Medium Green |
| Fruit Pattern (mature green stage) | Uniform | Uniform | Uniform |
| Shoulder color if different from base | n/a | n/a | n/a |
| Fruit color full ripe | Red | Red | Red |
| Flesh color full ripe | Red | Red | Red |
| Flesh color | Uniform | Uniform | Uniform |
| Locular gel color of table-ripe fruit | Yellow | Red | Red |
| Ripening | Uniform | Uniform | Uniform |
| Ripening | Uniformly | Uniformly | Uniformly |
| Stem Scar Size | Small | Small | Small |
| Core | Present | Coreless | Present |
| Epidermis Color | Yellow | Yellow | Yellow |
| Epidermis | Normal | Normal | Normal |
| Epidermis Texture | Average | Average | Tough |
| Thickness or Pericarp (mm) | 7.5 | 7 | 6.5 |
| Resistance to Fruit Disorder | Not tested | Not tested | Not tested |
| Disease and Pest Reactions | | | |
| Viral Diseases | | | |
| Cucumber Mosaic | n/t | n/t | n/t |
| Curly Top | n/t | n/t | n/t |
| Potato-y Virus | n/t | n/t | n/t |
| Blotch Ripening | n/t | n/t | n/t |
| Tobacco Mosaic Race 0 | n/t | n/t | n/t |
| Tobacco Mosaic Race 1 | n/t | n/t | n/t |
| Tobacco Mosaic Race 2 | n/t | n/t | n/t |
| Cracking, Concentric | n/t | n/t | n/t |
| Tobacco Mosaic Race 2[2] | n/t | n/t | n/t |
| Tomato Spotted Wilt | Resistant | Resistant | Susceptible |
| Tomato Yellows | n/t | n/t | n/t |
| Gold Fleck | n/t | n/t | n/t |
| Others | n/t | n/t | n/t |
| Bacterial Disease | | | |
| Bacterial Canker (Clavibacter michiganense) | Resistant | Min. resistant | Min. resistant |
| Bacterial Soft Rot (Erwinia carotovora) | n/t | n/t | n/t |
| Bacteria Speck (Pseudomonas tomato) | Susceptible | Resistant | Resistant |
| Bacterial Spot (Xanthomonas spp) | Resistant | Susceptible | susceptible |
| Bacterial Wilt (Ralstonia solanacearum) | Susceptible | Susceptible | Susceptible |
| Other Bacterial Disease | n/t | n/t | n/t |
| Fungal Disease | | | |
| Anthracnose (Colletotrichum spp.) | Susceptible | Susceptible | Susceptible |
| Brown Root Rot or Corky Root (Pyrenochaeta lycopersici) | Susceptible | Susceptible | Susceptible |
| Collar Rot or Stem Canker (Alternaria solani) | Susceptible | Susceptible | Susceptible |
| Early Blight Defoliation (Alternaria solani) | Intermediate Resistant | Min. resistant | Min. resistant |
| Fusarium Wilt Race 1 (F. oxysporum f. lycopersici) | Resistant | Resistant | Resistant |
| Fusarium Wilt Race 2 (F. oxysporum f. lycopersici) | Resistant | Resistant | Resistant |
| Fusarium Wilt Race 3 (F. oxysporum f. lycopersici) | Susceptible | Susceptible | Susceptible |
| Grey Leaf Spot (Stemphylium spp.) | n/t | n/t | n/t |
| Late Blight, race 0 (Phytophthora infestans) | Resistant | Susceptible | Susceptible |
| Late Blight, race 1 | Resistant | n/t | n/t |
| Leaf Mold race 1 (Cladosporium fulvum) | n/t | n/t | n/t |
| Leaf Mold race 2 (Cladosporium fulvum) | n/t | n/t | n/t |
| Leaf Mold race 3 (Cladosporium fulvum) | n/t | n/t | n/t |
| Leaf Mold Other Races | n/t | n/t | n/t |
| Nail head Spot (Alternaria tomato) | n/t | n/t | n/t |
| Septoria Leaf spot (S. Lycopersici) | n/t | n/t | n/t |
| Target Leaf spot (Corynespora cassiicola) | n/t | n/t | n/t |
| Verticillium Wilt Race 1 (V. dahliae race 1) | Resistant | Resistant | Resistant |
| Verticillium Wilt Race 2 (V. dahliae race 2) | Susceptible | Susceptible | Susceptible |
| Other Fungal Disease | n/t | n/t | n/t |
| Insects and Pests | | | |
| Colorado Potato Beetle (L. decemlineata) | n/t | n/t | n/t |
| Root Knot Nematode (M. sp.) | Resistant | Resistant | Resistant |
| Spider Mites (Tetranychus spp.) | n/t | n/t | n/t |
| Sugar Beet Army Worm (S. exigua) | n/t | n/t | n/t |
| Tobacco Flea Beetle (E. hiritipennis) | n/t | n/t | n/t |
| Tomato Hornworm (M. quinquemaculata) | n/t | n/t | n/t |
| Tomato Fruit worm (H. zea) | n/t | n/t | n/t |
| Whitefly (T. vaporariorum) | n/t | n/t | n/t |
| Other | n/t | n/t | n/t |

Chemistry and Composition of Full-Ripe Fruits

TABLE 2

Hot-break tomato juice characteristics for new variety 'H1766' and two check varieties 'H3402' and 'H1015'

| | 'H1766' | 'H3402' | 'H1015' |
|---|---|---|---|
| Serum viscosity (centistokes) | 10.07 | 7.40 | 8.78 |
| Juice Bostwick (cm) | 13.2 | 12.7 | 12.74 |
| Soluble solids (°Brix) | 5.5 | 5.2 | 5.3 |
| Lycopene (ppm) | 149 | 126 | 146 |

Average of 2 years of trials in California in a total of 29 locations.

TABLE 3

| Phenology | | | |
|---|---|---|---|
| | 'H1766' | 'H3402' | 'H1015' |
| Fruiting Season | short | short | short |
| Relative Maturity | early | medium | early |

TABLE 4

| Adaptation | | | |
|---|---|---|---|
| | 'H1766' | 'H3402' | 'H1015' |
| Culture | Field | Field | Field |
| Principle use | Whole-pack, Concentrated | Whole-pack, Concentrated | Whole-pack, Concentrated |
| Machine harvest | Yes | Yes | Yes |
| Regions of adaptability | | | |
| California Sacramento/ upper SJ valley | No | Yes -2 | Yes - 2 |
| California lower SJ valley | No | Yes -3 | Yes - 3 |
| Northeastern USA | Yes - 1 | Yes-1 | Yes - 1 |

If more than one categoary applies, they are listed in rank order.

Comparison of 'H1766' to Closest Varieties

Data in Tables 1, 2, 3, and 4 are based primarily upon trials conducted in Collegeville, Calif. from two replications, non-staked, in a research plot environment. Comparisons among varieties for processing traits (Table 2) were done over two years of side-by side testing throughout California. Disease resistance and adaptability assessments are based upon numerous observations collected throughout California and in regions/climates with specific disease pressure for ripe fruit rots, bacterial spot, bacterial canker, early blight, and late blight, including Ontario, Canada.

Several characteristics can distinguish 'H1766' from the similar commercial variety 'H3402'. The fruit size of 'H1766' is significantly larger and wider than 'H3402'; 'H1766' is approximately 11 grams heavier than 'H3402'. Furthermore, 'H1766' shows a wider adaptation to humid climates and has resistance to late blight.

Further Embodiments

Additional methods include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid. Accordingly, another aspect of the disclosure relates a method for producing an inbred tomato variety by: planting seed of the tomato variety 'H1766'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'H1766'. Tomato plants capable of expressing substantially all of the physiological and morphological characteristics of the parental inbred lines of tomato variety 'H1766' include tomato plants obtained by chasing selfs from seed of tomato variety 'H1766'.

One of ordinary skill in the art will recognize that once a breeder has obtained inbred tomato plants by chasing selfs from seed of tomato variety 'H1766', the breeder can then produce new inbred plants such as by sib-pollinating, or by crossing one of the identified inbred tomato plant with a plant of the tomato variety 'H1766'.

The disclosure further includes introducing one or more desired traits into the tomato variety 'H1766'. For example, the desired trait may include male sterility, male fertility, herbicide resistance, insect resistance, disease resistance, and drought resistance.

The desired trait may be found on a single gene or combination of genes. The desired trait may be a genetic locus that is a dominant or recessive allele. The genetic locus may be a naturally occurring tomato gene introduced into the genome of a parent of the variety by backcrossing, a natural or induced mutation, or a transgene introduced through genetic transformation techniques. For a genetic locus introduced through transformation, the genetic locus may comprise one or more transgenes integrated at a single chromosomal location. Accordingly, the disclosure provides tomato plants or parts thereof that have been transformed with one or more transgenes (i.e., a genetic locus comprising a sequence introduced into the genome of a tomato plant by transformation) to provide a desired trait. In one aspect, the one or more transgenes are operably linked to at least one regulatory element.

The gene(s) may be introduced to tomato variety 'H1766' through a variety of well-known techniques, including for example, molecular biological, other genetic engineering, or plant breeding techniques, such as recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) (also referred to as Microsatellites)), enhanced selection, genetic marker enhanced selection, and transformation. Accordingly, tomato seed, plants, and parts thereof produced by such genetic engineering or plant breed techniques are also part of the present disclosure.

Also provided herein are single locus converted plants and seeds developed by backcrossing wherein essentially all of the morphological and physiological characteristics of an inbred are recovered in addition to the characteristics conferred by the single locus transferred into the inbred via the backcrossing technique. A single locus may comprise one gene, or in the case of transgenic plants, one or more transgenes integrated into the host genome at a single site (locus). One or more locus conversion traits may be introduced into a single tomato variety.

DEPOSIT INFORMATION

A deposit of the tomato variety 'H1766' is maintained by HeinzSeed Company, having an address at 6755 CE Dixon St, Stockton, Calif. 95206, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the American Type Culture Collection (ATCC), P.O. Box 1549, MANASSAS, Va. 20108 USA.

At least 2500 seeds of tomato variety 'H1766' were deposited on Dec. 12, 2017 according to the Budapest Treaty in the American Type Culture Collection (ATCC), P.O. Box 1549, MANASSAS, Va. 20108 USA. The deposit has been assigned ATCC number PTA-124676. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed for the enforceable life of the patent.

The deposits will be maintained in the ATCC depository, which is a public depository, for a period of 30 years, or 5 years after the most recent request, or for the effective life of the patent, whichever is longer, and will be replaced if a deposit becomes nonviable during that period.

What is claimed is:

1. Tomato seed designated as 'H1766', representative sample of seed having been deposited under ATCC Accession Number PTA-124676.

2. A plant produced by growing the seed of claim 1.

3. A plant part from the plant of claim 2, wherein the plant part comprises at least one cell from tomato variety 'H1766'.

4. The plant part of claim 3, wherein the part is selected from the group consisting of leaf, ovule, pollen, cell, rootstock, scion, fruit, cotyledon, meristem, anther, root, root tip, pistil, flower, stem, calli, stalk, hypocotyl, pericarp, and portion thereof.

5. A tomato plant having all the physiological and morphological characteristics of the tomato plant of claim 2.

6. A plant part from the plant of claim 5, wherein the plant part comprises at least one cell from tomato variety 'H1766'.

7. The plant part of claim 6, wherein the part is selected from the group consisting of leaf, ovule, pollen, cell, rootstock, scion, fruit, cotyledon, meristem, anther, root, root tip, pistil, flower, stem, calli, stalk, hypocotyl, pericarp, and portion thereof.

8. A tomato plant having all the physiological and morphological characteristics of tomato variety 'H1766', wherein a representative sample of seed has been deposited under ATCC Accession Number PTA-124676.

9. A plant part from the plant of claim 8, wherein the plant part comprises at least one cell from tomato variety 'H1766'.

10. The plant part of claim 9, wherein the part is selected from the group consisting of leaf, ovule, pollen, cell, rootstock, scion, fruit, cotyledon, meristem, anther, root, root tip, pistil, flower, stem, calli, stalk, hypocotyl, pericarp, and portion thereof.

11. Pollen of the plant of claim 2.

12. An ovule of the plant of claim 2.

13. A tissue culture of regenerable cells from a plant part of claim 3, wherein said tissue culture of regenerable cells has all the physiological and morphological characteristics of tomato variety 'H1766'.

14. A tomato plant regenerated from the tissue culture of claim 13, the plant having all the physiological and morphological characteristics of tomato variety 'H1766', wherein a representative sample of seed has been deposited under ATCC Accession Number PTA-124676.

15. A protoplast produced from the tissue culture of claim 13, wherein a plant regenerated from the protoplast has all the physiological and morphological characteristics of tomato variety 'H1766'.

16. A method of producing a tomato plant derived from tomato variety 'H1766', the method comprising crossing the plant of claim 2 with another tomato plant to produce a $F_1$ hybrid tomato plant.

17. The method of claim 16, further comprising harvesting seed from the $F_1$ hybrid tomato plant.

18. The method of claim 16, further comprising crossing the $F_1$ hybrid tomato plant with itself or another plant to produce seed from a progeny plant.

19. The plant of claim 2, further comprising a transgene.

20. The plant of claim 2, further comprising a single locus conversion.

21. A method of making seeds from tomato variety 'H1766', the method comprising selecting seeds from a cross of one 'H1766' plant with another 'H1766' plant, a sample of 'H1766' tomato seed having been deposited under ATCC Accession Number PTA-124676.

22. A method for producing a tomato fruit, the method comprising:
   growing the tomato plant of claim 2 to produce a tomato fruit; and
   harvesting the tomato fruit.

23. A method for producing a tomato seed comprising:
   self-pollinating the tomato plant of claim 2; and
   harvesting the resultant tomato seed.

24. A method of vegetatively propagating the plant of claim 2, the method comprising:
   obtaining a part of the plant; and
   regenerating a plant from the part, the regenerated plant having all the physiological and morphological characteristics of tomato variety 'H1766'.

* * * * *